(12) United States Patent
Martin et al.

(10) Patent No.: US 7,098,325 B2
(45) Date of Patent: Aug. 29, 2006

(54) PROCESS FOR THE SULFURIZATION OF A PHOSPHORUS-CONTAINING COMPOUND

(76) Inventors: Pierre Martin, Meisenweg 38, Rheinfelden (CH) CH-4310; Francois J Natt, Traugott Meyer-Strasse 3, Aesch (CH) CH-4147

( * ) Notice: Subject to any disclaimer, the term of this patent is extended or adjusted under 35 U.S.C. 154(b) by 389 days.

(21) Appl. No.: 10/266,027

(22) Filed: Oct. 7, 2002

(65) Prior Publication Data

US 2003/0139592 A1    Jul. 24, 2003

Related U.S. Application Data

(63) Continuation of application No. 09/416,031, filed on Oct. 12, 1999, now abandoned, which is a continuation-in-part of application No. 09/168,447, filed on Oct. 8, 1998, now abandoned.

(51) Int. Cl.
*C07H 21/00* (2006.01)
*C07D 417/00* (2006.01)
*C07D 285/08* (2006.01)

(52) U.S. Cl. ............ 536/25.3; 536/25.34; 548/123; 548/128

(58) Field of Classification Search .......... 536/25.3, 536/25.34; 548/123, 128
See application file for complete search history.

(56) References Cited

U.S. PATENT DOCUMENTS 5,003,097 A    3/1991    Beaucage et al.

6,096,881 A  *  8/2000  Han et al. .................. 536/25.3

FOREIGN PATENT DOCUMENTS

WO    WO 97 41130 A    11/1997
WO    WO 98 54198 A    12/1998

OTHER PUBLICATIONS

Chemical Abstract 1974:107961 CAPLUS -Full-text.
Chemical Abstracts 83:193333.

* cited by examiner

*Primary Examiner*—Shaojia Anna Jiang
*Assistant Examiner*—Traviss C. McIntosh
(74) *Attorney, Agent, or Firm*—Novartis

(57) ABSTRACT

The invention relates to a process for the sulfurization of phosphorus-containing compounds which comprises contacting the phosphorus compound to be sulfurized with a sulfur transfer reagent of formula (I)

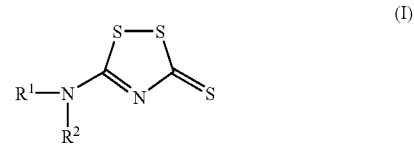

wherein
$R^1$ is aryl which can be substituted by halo, $(C_1-C_6)$ alkyl or $(C_1-C_6)$ alkoxy, and
$R^2$ is $(C_1-C_6)$ alkyl, which could also form a cyclic ring together with $R^1$, in a solvent or a mixture of solvents.

12 Claims, No Drawings

PROCESS FOR THE SULFURIZATION OF A PHOSPHORUS-CONTAINING COMPOUND

This application is a continuation of U.S. application Ser. No. 09/416,031, filed Oct. 12, 1999, now abandoned, which is a continuation-in-part of U.S. application Ser. No. 09/168,447, filed Oct. 8, 1998, now abandoned.

Phosphorothioate analogues of the phosphate moiety in compounds are of great interest in nucleic acid research, protein research, etc. For example, phosphorothioate-containing antisense oligonucleotides have been used in vitro and in vivo as inhibitors of gene expression.

Introduction of phosphorothioate moieties into oligonucleotides, assembled by solid-phase synthesis, can be achieved using either an H-phosphonate approach or a phosphoramidite approach. The H-phosphonate approach involves a single sulfur transfer step, carried out after the desired sequence has been assembled, to convert all of the internucleotide linkages to phosphorothioates. Alternatively, the phosphoramidite approach features a choice at each synthetic cycle: a standard oxidation provides the normal phosphordiester internucleotide linkage, whereas a sulfurization step introduces a phosphorothioate at the specific position in the sequence. An advantage of using phosphoroamidite chemistry, therefore, is the capability to control the state of each linkage in a site specific manner.

The success of the phosphoramidite approach is dependent on the availability of efficient, good soluble sulfurization reagents that are compatible with automated DNA synthesis. A number of reagents have been designed and tested in recent years (WO 97/41130) but none of them is able to fulfil all the requirements for an ideal sufurization reagent: excellent yields, good solubility, stable solutions, short reaction times, no formation of P=O units, no further reagents necessary, no side reactions with other parts of the molecule, odourless itself and odourless reaction products, capable of regeneration, easily available.

The present invention provides a process for the sulfurization of phosphorus-containing compounds. This process involves contacting the compound to be sulfurized with a sulfur transfer reagent of formula (I)

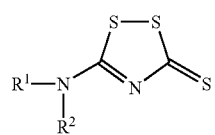

(I)

wherein $R^1$ is aryl which can be substituted by halo, $(C_1-C_6)$ alkyl or $(C_1-C_6)$ alkoxy, and $R^2$ is $(C_1-C_6)$ alkyl, which could also form a cyclic ring together with $R^1$.

Preferred are sulfur transfer reagents of formula (I) wherein $R^1$ is phenyl, tolyl, xylyl, naphthyl, 4-chlorophenyl or anisyl, and $R^2$ is methyl, ethyl, propyl or isopropyl.

Also preferred are sulfur transfer reagents of formula (II)

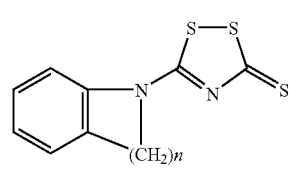

(II)

wherein n is 2 or 3.

The method of the present invention typically involves contacting a sulfur transfer reagent of formula (I) with a phosphorus-containing compound in solution or on a solid support, in a solvent or a mixture of solvents. The phosphorus in the phosphorus-containing compound is typically a trivalent phosphorus. Upon sulfurization it becomes a pentavalent phosphorus. The trivalent phosphorus can be a phosphite, phosphonite, phosphonamidite, phosphine or any other phosphorus (III) derivative as part of the synthesis of DNA, RNA, phosphoropeptides, phosphonopeptides, phosphorylated nucleoside sugars or oligosaccharides.

Preferably, the phosphorus containing compound is a compound of formula (III)

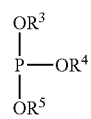

(III)

wherein each of $R^3$ and $R^4$ is a nucleoside or an oligonucleotide, and $R^5$ is a protective group. Preferably, $R^5$ is —$CH_2CH_2CN$, —$CH_2$—CH=CH—$CH_2CN$, —$CH_2CH_2$-4-nitrophenyl or —$CH_2CH$=$CH_2$.

For oligonucleotides, the sulfur transfer reagents of formula (I) or (II) do not modify the nucleosidic residues, thereby preserving the genetic identity of the macromolecule. Thus, the reagents of formula (I) or (II) and the process of the present invention can be reliably used in the automated synthesis of desired compounds. For example, the process is very useful for the automated synthesis up to gram scales of oligonucleotides, including both oligodeoxyribonucleotides and oligoribonucleotides of length from 4 to 50 bases containing the phosphorothioate substitution at either a single site or at all positions. Typically, an amount of 1–30 molar equivalents, more preferably 2–10 molar equivalents, of the sulfur transfer reagent of formula (I) or (II) is used relative to the amount of the trivalent phosphorus groups in the phosphorus-containing compound. The reaction is typically carried out under an inert atmosphere, such as argon, although this is not required.

The sulfurization reaction occurs in a solvent. The solvent can be a hydrocarbon solvent, ethereal solvent, nitrile solvent, chlorinated solvent, heterocyclic solvent etc. Specific examples of suitable solvents include pyridine, N,N-dimethylformamide (DMF), tetrahydrofuran (THF), acetonitrile and methylene chloride. Preferably, acetonitrile is used.

Although the reaction can be carried out at room temperature, it may also be carried out within a temperature range of about 0–50° C., and preferably 10–50° C. Typically, the conversion to the thioated compound is greater than 95%, mostly greater than about 99%.

A great advantage of the process of the present invention is that the compounds of formula (I) or (II) could be easily recovered from the reaction solution obtained from the automated synthesizer by reacting these solutions with sulfur or sulfur transfer reagents. In contrast, such recycling is not possible with the compounds described in WO 97/41130. Furthermore, the sulfurization reaction described therein (see page 15 of WO 97/41130) leads to the formation of carbonoxysulfide (COS) which is an easily flammable gas with a horrible odor. This formation of COS causes practical and safety problems.

The compounds of formulae (I) and (II) could be prepared by the reaction of the corresponding thioureas with $CS_2$ and subsequent oxidation (DT 2404477 A1). The following examples illustrate the invention but do not restrict it in any manner.

EXAMPLES

Preparation of the Thioureas

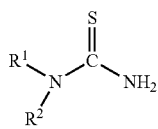

N-Ethylphenyl-thiourea ($R^1$=phenyl, $R^2$=ethyl)

A solution of 35.0 g (0.288 mol) of ethylaniline and 46.8 g (0.577 mol) of NaSCN in 220 ml toluene is heated to 50° C. and a mixture of 31 ml trifluoroacetic acid and 45 ml toluene is added over a period 3.5 h. The reaction mixture is then refluxed for 25 h. After cooling, the mixture is washed with water, dried and evaporated. The residue is treated with ether. After filtration, a beige powder is obtained, mp. 104 to 105° C.

The following analogues are prepared:

| $R^1$ | $R^2$ | MP (° C.) | MS (M+) |
|---|---|---|---|
| 2,3-dimethylphenyl | ethyl | 93–94 | 208 |
| 4-methoxyphenyl | methyl | 126 | 196 |
| 1-naphthyl | ethyl | 124–125 | 230 |
| phenyl | methyl | 105–106 | 166 |
| 4-chlorophenyl | methyl | 125 | 200/202 |
| indoline | | 156 | 178 |
| tetrahydrochinoline | | 134–135 | 192 |

Preparation of Compounds of Formula (I)

Method A)

Preparation of N-ethyl,N-phenyl-5-amino-3H-1,2,4-dithiazol-3-thione ($R^1$=Phenyl, $R^2$=ethyl)

To a stirred mixture of 29.52 g (0.164 mmol) of N-ethyl-phenyl-thiourea, 14.9 g of $CS_2$ and 400 ml THF is added 8.17 g (0.34 mol) of NaH, in portions. After the production of hydrogen has ceased, the reaction mixture is heated for 2.5 h. After cooling, the precipitate is filtered, dissolved in 300 ml $H_2O$ and a solution of 41.56 g $I_2$ and 81.55 g KI in 500 ml $H_2O$ is added dropwise. The formed precipitate is filtered off and washed with hexane. Obtained are yellow crystals, mp 141° C.

Method B)

To a solution of 11.1 mmol of thiourea in 20 ml DMSO, 0.87 ml $CS_2$ and 1.56 g powdered KOH are added. After stirring for 24 h, the reaction mixture is poured into water and extracted with EtOAc. The extract is washed with water, dried ($Na_2SO_4$) and evaporated. The residue is chromatographed ($SiO_2$, hexane:EtOAc 6:1).

The following analogues (method A or B) are prepared:

| $R^1$ | $R^2$ | MS (M+) |
|---|---|---|
| 2,3-dimethylphenyl | ethyl | 282 |
| 4-methoxyphenyl | methyl | 270 |
| naphthyl | ethyl | 304 |
| phenyl | methyl | 240 |
| 4-chlorophenyl | methyl | 274/276 |
| indoline | | 252 |
| tetrahydrochinoline | | 266 |

Sulfurization Reaction

A) Reaction in Solution

To a solution of 0.786 mmol sulfurization reagent of formula (I) in 20 ml $CD_3CN$, 131 mg (0.786 mmol) $P(OEt)_3$ are added. Immediately, a sample of the reaction mixture is analyzed with $^{31}P$-NMR-spectrometry. Only one singulett at 68.587 ppm can be observed for $(EtO)_3P=S$, no signals at 18 ppm (mixed anhydride) and 0 ppm $(EtO)_3P=O$ can be detected. The $^{13}C$-NMR -spectrum of a second sample shows no signals above 200 ppm, which means that no $CS_2$ is formed during the reaction.

B) Synthesis of Phosphorothioate Containing Oligonucleotides

For 1 µmole scale syntheses, a Perseptive Expedite MOSS synthesizer is used. The syntheses are performed on Polystyrene Primer support (Pharmacia) loaded with the 3' end residue. Solutions at 0.05M in acetonitrile of β-cyanoethyl deoxyribonucleosides phosphoramidites (Perseptive) or β-cyanoethyl 2'-methoxyethylribonucleosides phosphoramidites (P. Martin, Helvetica Chimica Acta, 78 (1995), 486–504) are used. In the coupling step, phosphoramidites are activated by benzimidazolium triflate (0.2M in acetonitrile; R. Noyori, J. Org. Chem. 61, 1996, 7996–7997). Non sulfurized phosphodiesters are oxidized by anhydrous t-butyl hydroperoxide (0.5M in toluene; this solution is obtained by diluting the toluene solution of t-butyl hydroperoxide from Lipomed). Capping and washing steps are carried out by standard reagents and solvents.

Typical cycles as well as the sulfurization conditions are shown in Table 1. The sulfur transfer reagent was used at a 0.1M concentration in acetonitrile. The volume of sulfurization reagent was 1.28 ml (including prime and purge volumes). Total contact time was 2 minutes.

Upon completion of solid-phase steps, the oligonucleotides (5' trityl-off) are cleaved from the support and deprotected with 30% ammonium hydroxide (2 h at room temperature for polypyrimidines and at 80° C. for mixed sequences), desalted on NAP-10 columns (Pharmacia) and analyzed by capillary gel electrophoresis and Maldi-Tof MS (see Table 2). Alternatively, the same process is applicable to trityl-on oligonucleotides suited for RP-HPLC purification.

TABLE 1

Synthetic conditions

| Step | Reagent/Solvent | Function | Time in sec. per cycle (repeat) |
|---|---|---|---|
| 1 | MeCN | Wash | 20 (2x) |
| 2 | 3% CCl$_3$COOH/CH$_2$Cl$_2$ | Detritylation | 20 + 40 |
| 3 | MeCN | Wash | 20 (2x) |
| 4 | Nucleotide/tetrazole/MeCN | Coupling | 180 |
| 5 | MeCN | Wash | 20 (2x) |
| 6 | PM-5468 0.1M in acetonitrile or 0.5M tBuOOH in DCM | Sulfurization/Oxidation | 20 (2x) |
| 7 | MeCN | Wash | 20 (2x) |
| 8 | Ac$_2$O/lutidine/NMI/THF | Capping | 10 + 20 |
| 9 | MeCN | Wash | 20 (2x) |

TABLE 2

Sequences and results (N: DNA; n: 2'-methoxyethyl RNA; s: phosphorothioate)

| Sequence | MW$_{calc.}$ | MW$_{meas.}$ |
|---|---|---|
| TsTT TTT TT | 2387.7 | 2387.7 |
| TTT TsTT TT | 2387.7 | 2386.5 |
| tstt ttt tt | 2980.4 | 2984.8 |
| ttt tstt tt | 2980.4 | 2985.6 |
| AsAsTs CsCsTs CsCsCs CsCsAs GsTsTs CsAsCs CsC | 6223.2 | 6222.8 |

C) Solid Phase Synthesis of a 20-mer Full Phosphorothiate Oligodeoxyribonucleotide Syntheses are performed on a Pharmacia OligoPilot II using 6.3 ml (150–200 μmole scale) or 24 ml (500 μmole scale) columns. Same reagents are used as in example B except for the support (Primer 30 HL loaded with the first 3' deoxyribonucleoside via a succinyl linker) and the phosphoramidites are dissolved as a 0.2M solution in acetonitrile.

Synthesis scale is based on weight and loading of the support. Excess and crude yields are calculated from the synthesis scale.

1.5 equivalent DNA phosphoramidite and the same excess of benzimidazolium triflate are simultaneously added to the column and recycled for 3 minutes. The synthetic conditions are shown in Table 3. The specific conditions for the sulfurization as well as the results are shown in Table 4. Crude material contained between 67 and 72% of full length material.

TABLE 3

Synthetic conditions on the OligoPilot II (Pharmacia)

| Step | Reagent/Solvent | Function | Volume or equiv. |
|---|---|---|---|
| 1 | MeCN | Wash | 6 CV |
| 2 | 3% CCl$_3$COOH/CH$_2$Cl$_2$ | Detritylation | 6 CV |
| 3 | MeCN | Wash | 6 CV |
| 4 | Nucleotide/tetrazole/MeCN | Coupling | 1.5 equiv |
| 5 | MeCN | Wash | 6 CV |
| 6 | STR | Sulfurization | See Table 4 |
| 7 | MeCN | Wash | 6 CV |
| 8 | Ac$_2$O/lutidine/NMI/THF | Capping | 0.5 CV; 0.5 min. |
| 9 | MeCN | Wash | 6 CV |

TABLE 4

Synthesis of the 20-mer phosphorothioate 1 5'-AsAsTs CsCsTs CsCsCs CsCsAs GsTsTs CsAsCs CsC and the 20-mer chimeric 2'-methoxyethyl RNA/DNA phosphorothioate 2 5'-GsTsGs AsGsGs CsCsCs TsGsts tsgsas gststs gsg (n is 2'-methoxyethyl residue, N is DNA residue, s is phosphorothioate)

| OLIGO | STR | Solvent | Conc.(M) | Excess | Crude yield | P=O ($^{31}$P-NMR) |
|---|---|---|---|---|---|---|
| 1 | Van Boom | CH3CN/ Picoline | 0.5 | 8 | 63.6% | <0.5% |
| 1 | Van Boom | CH3CN/ Picoline | 0.5 | 4 | 60.4% | <0.5% |
| 1 | PM-5468 | CH3CN | 0.1 | 8 | 66.5% | <0.5% |
| 1 | PM-5468 | CH3CN | 0.1 | 4 | 68.8% | <0.5% |

TABLE 4-continued

Synthesis of the 20-mer phosphorothioate 1 5'-AsAsTs CsCsTs CsCsCs CsCsAs GsTsTs CsAsCs CsC and the 20-mer chimeric 2'-methoxyethyl RNA/DNA phosphorothioate 2 5'-GsTsGs AsGsGs CsCsCs TsGsts tsgsas gststs gsg (n is 2'-methoxyethyl residue, N is DNA residue, s is phosphorothioate)

| OLIGO | STR | Solvent | Conc.(M) | Excess | Crude yield | P=O ($^{31}$P-NMR) |
|---|---|---|---|---|---|---|
| 1 | PM-5468 | THF | 0.2 | 4 | 68% | <0.5% |
| 2 | PM-5468 | CH3CN | 0.1 | 4 | 82% | <0.5% |

Abbreviations:
STR: Sulfer Transfer reagent
PM-5468: Compound of formula (I) wherein $R^1$ is phenyl and $R^2$ is ethyl
Van Boom: Phenyl Acetyl DiSulfide also named as PADS.
BT: Benzimidazolium Triflate Recyling of the Reagent from the Solutions Obtained After the Sulfurization Step at the Synthesizer Method A)

To the solutions collected after the sufurization step from the synthesizer, sulfur or sulfur dissolved in $CS_2$ is added. After 2 days, the solutions are filtered and evaporated. The residue is dissolved in EtOAc and filtered over a short $SiO_2$-column. After evaporation and washing of the residue with hexane, pure compounds of formula (I) are obtained.

Method B)

The solutions collected after the sufurization step from the synthesizer are evaporated. To the solution of the residue in acetone, sulfur is added and the mixture is refluxed for 2 h and evaporated. The residue is treated with acetonitrile, filtered, evaporated and chromatographed. Pure compounds of formula (I) are obtained.

Example

Comparison of Sulfurization Efficiencies of Three Sulfur Transfer Reagents

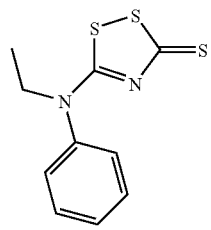

A

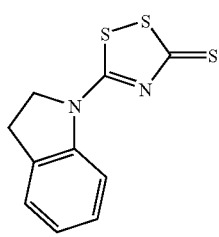

B

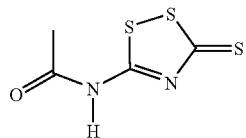

C

The purpose of this experiment is the head to head comparison of the three mentioned sulfur transfer reagents (namely, A, B, C), the third being described in Patent WO98/54198. In this reference, compound C is used for the preparation of phosphorothioate oligonucleotides with a 0.02M (12 equiv.)solution in pyridine/acetonitrile (1:9). As the use of pyridine and the high excess required for this experiment are considered to be drawbacks of a STR, we compared the three reagents with "ideal" or satisfactory conditions. Compound C is not soluble at 0.1 M in acetonitrile nor THF which are the recommended conditions for compounds A and B The test sequence is a polythymidine (12-mer) where in the middle of the sequence, the residue to be sulfurized is a 2'-O-methoxyethyl thymidine. The sulfurization is carried out with 0.02M (2 equiv.) in acetonitrile for 2 min. When specified, the support is subsequently exposed to oxidation for further conversion of phosphite species The crude solutions are analyzed by Maldi-Tof MS, CGE and IE-HPLC, and the results are summarized in Table 5.

TABLE 5

Analyses of crude oligonucleotide TTT TTts TTT TTT

| entry | STR | Crude yield (OD) | % CGE | % P=O (IE-HPLC)[b] | Maldi-T of MS (MWcalc. = 3678.6) |
|---|---|---|---|---|---|
| 1 | A | 97 | 98.2 | n.d. | 3676.9 |
| 2 | B | 91 | 97.5 | n.d. | 3677.2 |
| 3 | C | 88 | 73.3 | 10[c] | 3675.7; 3280.6; 1896.5; 1757.7 |
| 4 | A[a] | 95 | 98.8 | n.d. | 3676.6 |
| 5 | C[a] | 90 | 97.8 | 17.7 | 3676.6 |

[a] sulfurization is followed by a oxidation with tBuOOH as already described
[b] not detected
[c] 7.8% of cleavage products Discussion Both STR A and B sulfurize the 2'-O-methoxyethyl residue in a satisfactory yield.

Under these conditions, it appears that STR C does not sulfurize completely the internucleotidic bridge which leads a) to a partial cleavage of the remaining phosphite during detritylation following the sulfurization and b) to the oxidation of the non cleaved phosphite in the next chain elongation cycle.

When the sulfurization is followed by an additional oxidation before further chain elongation (entry 5), no cleavage product is observed, but the IE-HPLC analysis shows a much higher P=O content than the corresponding experiment with STR A.

The invention claimed is:

1. A process for the sulfurization of phosphorus-containing compounds which comprises contacting the phosphorus compound to be sulfurized with a sulfur transfer reagent of formula (I)

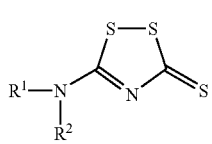

(I)

wherein $R^1$ is aryl which can be substituted by halo, ($C_1$–$C_6$) alkyl or ($C_1$–$C_6$) alkoxy, and $R^2$ is ($C_1$–$C_6$) alkyl, which could also form a cyclic ring together with $R^1$.

2. A process according to claim 1 wherein $R^1$ is phenyl, tolyl, xylyl, naphthyl, 4-chlorophenyl or anisyl, and $R^2$ is methyl, ethyl, propyl or isopropyl.

3. A process according to claim 1 wherein the sulfur transfer reagent is a compound of formula (II)

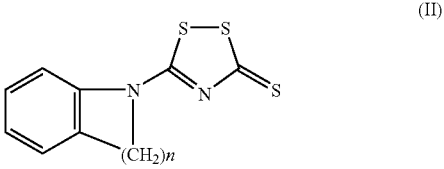

(II)

wherein n is 2 or 3.

4. A process according to claim 1 wherein the phophorus-containing compound is a trivalent phosphorus compound.

5. A process according to claim 4 wherein the trivalent phosphorus compound is a compound of formula (III)

(III)

wherein each of $R^3$ and $R^4$ is a nucleoside or an oligonucleotide, and $R^5$ is a protective group.

6. A process according to claim 5 wherein $R^5$ is —$CH_2CH_2CN$, —$CH_2$—CH=CH—$CH_2CN$, —$CH_2CH_2$-4-nitrophenyl or —$CH_2CH$=$CH_2$.

7. A process according to claim 1 wherein the sulfur transfer reagent is used in an amount of 1–30 molar equivalents, relative to the amount of the phosphorus compound.

8. A process according to claim 1 wherein the reaction is carried out in the presence of a solvent selected from pyridine, DMF, THF, acetonitrile and methylene chloride.

9. A process according to claim 2 wherein the phosphorus-containing compound is a trivalent phosphorus compound.

10. A process according to claim 3 wherein the phosphorus-containing compound is a trivalent phosphorus compound.

11. A process according to claim 7 wherein the sulfur transfer reagent is used in an amount of 2–10 molar equivalents.

12. A process according to claim 8 wherein the solvent is acetonitrile.

* * * * *